US00PP29114P3

(12) United States Plant Patent
Park

(10) Patent No.: US PP29,114 P3
(45) Date of Patent: Mar. 13, 2018

(54) ***COREOPSIS* PLANT NAMED 'URIBL01'**

(50) Latin Name: ***Coreopsis rosea*×*Coreopsis verticillata***
Varietal Denomination: URIBL01

(71) Applicant: Uriseed Institute, Icheon-si (KR)

(72) Inventor: Kong Young Park, Icheon-si (KR)

(73) Assignee: URISEED INSTITUTE, Icheon-si (KR)

( * ) Notice: Subject to any disclaimer, the term of this patent is extended or adjusted under 35 U.S.C. 154(b) by 0 days.

(21) Appl. No.: 14/999,120

(22) Filed: Mar. 31, 2016

(65) Prior Publication Data

US 2017/0049028 P1 Feb. 16, 2017

(30) Foreign Application Priority Data

Aug. 14, 2015 (QZ) ..... PBR 20151903

(51) Int. Cl.
*A01H 5/02* (2006.01)

(52) U.S. Cl.
USPC ..... Plt./417

(58) Field of Classification Search
USPC ..... Plt./417
CPC ..... A01H 5/025; A01H 5/02; A01H 5/00
See application file for complete search history.

(56) References Cited

U.S. PATENT DOCUMENTS

PP15,455 P3 * 12/2004 Faria ..... Plt./417

OTHER PUBLICATIONS

Jala Morphological Change Due to Effects of Acute Gamma Ray on Wishbone Flower (*Torenia fourmieri*) in Vitro, 2011 International Transaction Journal of Engineering, Management, & Applied Sciences & Technologies, vol. 2 No. 4, 375-383.*
Park et al. Development of a New *Coreopsis* Variety 'Uridream Pink' by Gamma-ray Irradiation, Kor. J. Hort. Sci. Technol. 32(6):906-911, 2014.*
English translation of Park et al. 2017, 16 pp.*

* cited by examiner

*Primary Examiner* — June Hwu
(74) *Attorney, Agent, or Firm* — Penny J. Aguirre

(57) ABSTRACT

A new cultivar of hybrid *Coreopsis* plant named, 'URIBL01', that is characterized by its dwarf plant habit, its large inflorescences, its ray florets that are crimson red in color, and its disk florets that are orange-yellow in color.

2 Drawing Sheets

Botanical classification: *Coreopsis rosea*×*Coreopsis verticillata.*

Variety denomination: 'URIBL01'.

CROSS REFERENCE TO RELATED APPLICATIONS

This application is co-pending with U.S. Plant Patent Applications filed for plants derived from the same breeding program that is entitled *Coreopsis* Plant Named 'URIBL02' (U.S. Plant patent application Ser. No. 14/999,137).

BACKGROUND OF THE INVENTION

The present invention relates to a new and distinct cultivar of *Coreopsis* plant, botanically of hybrid origin and known as *Coreopsis* 'URIBL01' and will be referred to hereinafter by its cultivar name, 'URIBL01'. The new cultivar of *Coreopsis* is an herbaceous perennial grown for landscape and container use.

The new invention arose from an ongoing controlled breeding program in Icheon-si, Korea. The objective of the breeding program is to develop hybrid cultivars of *Coreopsis* with unique flower colors and dwarf plant habit.

The new cultivar arose as a mutation using gamma radiation of un-rooted cuttings of unknown, unnamed proprietary plants from the Inventor's breeding program in January of 2010. 'Limerock Ruby' (U.S. Plant Pat. No. 15,455) and addition cultivars were initially used in the breeding program in prior years to obtain initial primary mutations and subsequent rounds of gamma radiation of preformed on proprietary seedlings until 'URIBL01' was selected in September 2010 as a single unique plant amongst the resulting mutated seedlings.

Asexual propagation of the new cultivar was first accomplished by stem cuttings by the Inventor in Icheon-si, Korea in September of 2010. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'URIBL01' as unique cultivar of *Coreopsis*.

1. 'URIBL01' exhibits a dwarf plant habit.
2. 'URIBL01' exhibits large inflorescences.
3. 'URIBL01' exhibits ray florets that are crimson red in color.
4. 'URIBL01' exhibits disk florets that are orange-yellow in color.

'URIBL01' can be most closely compared to 'URIBL02' and 'Limerock Ruby'. 'Limerock Ruby', is similar to 'URIBL01' in having ray florets that are crimson red in color. 'Limerock Ruby' differs from 'URIBL01' in having a plant height that is 50% taller, in having a wider plant spread, and in having smaller inflorescences with smaller ray florets. 'URIBL02' is similar to 'URIBL01' in having a dwarf plant habit. 'URIBL02' differs from 'URIBL01' in having ray florets that are light red-purple in color, in having a slightly larger plant height and width, and in having inflorescences that are slightly larger in size.

BRIEF DESCRIPTION OF THE DRAWINGS

The accompanying colored photographs illustrate the overall appearance and distinct characteristics of the new *Coreopsis*. The photographs were taken of a 3 month-old plant of 'URIBL01' as grown outdoors in Boskoop, The Netherlands.

The photograph in FIG. 1 provides a side view of a plant of 'URIBL01' in bloom.

Figure 1:
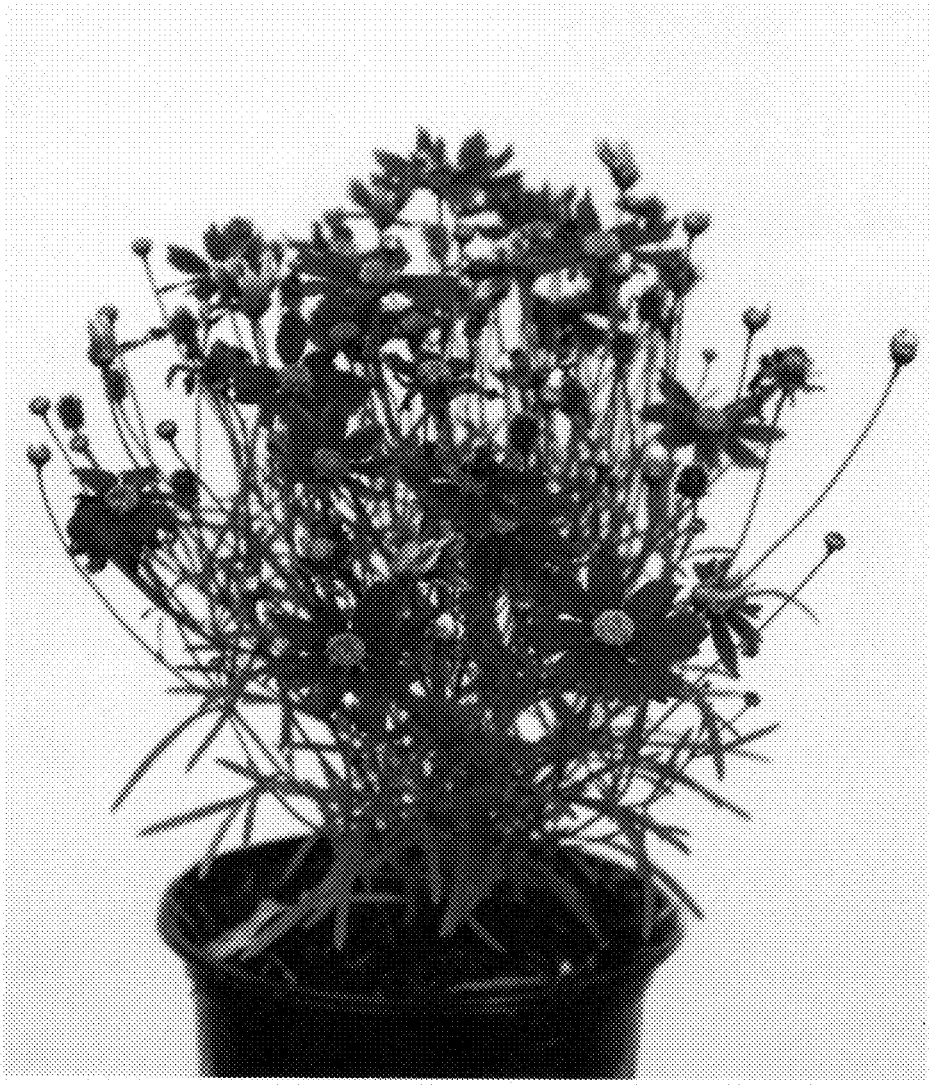
Figure 2:
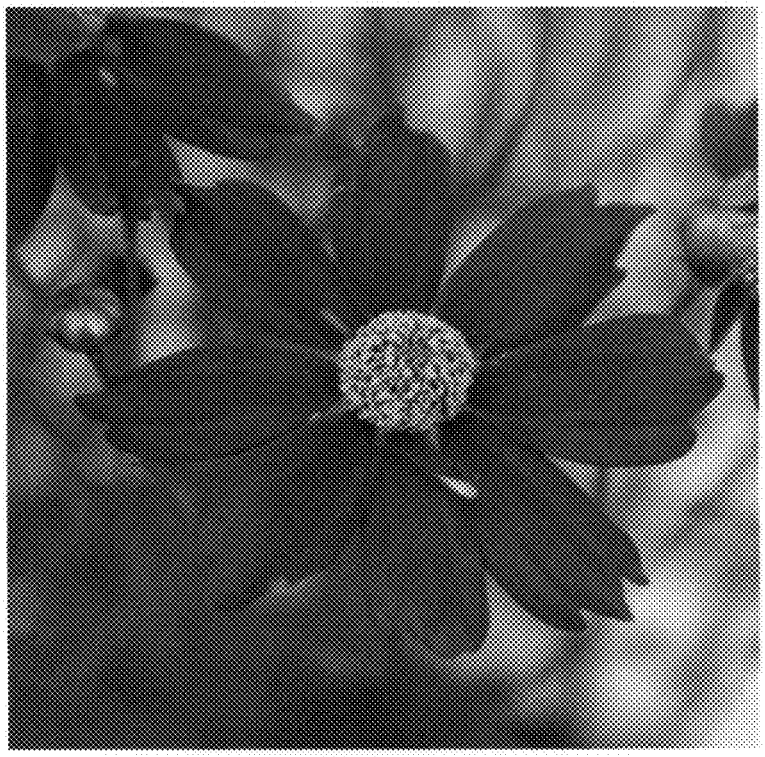

The photograph in FIG. 2 provides a close-up view of an inflorescence of 'URIBL01'.

Figure 3:
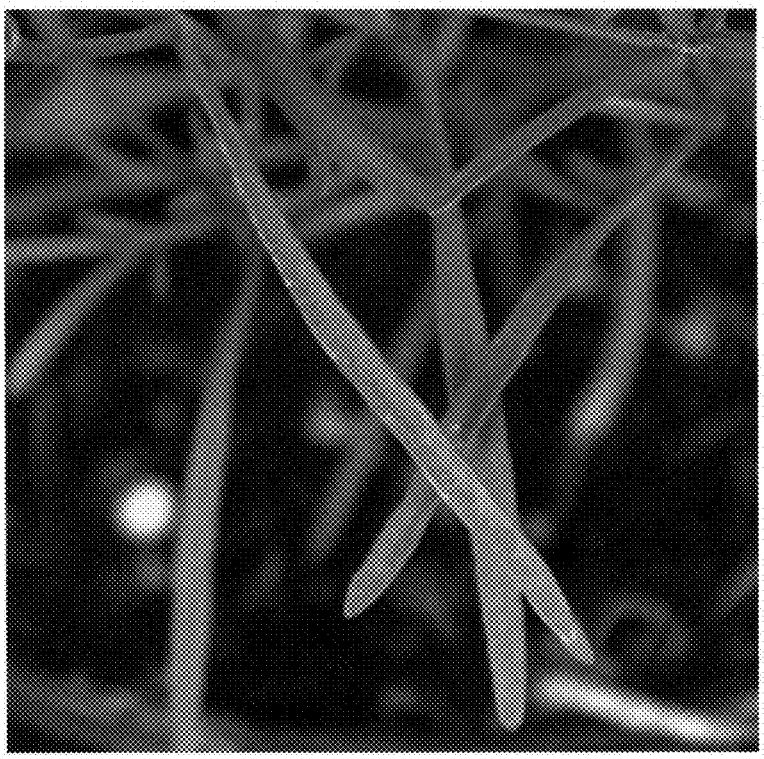

The photograph in FIG. 3 provides a close-up view of the foliage of 'URIBL01'.

The colors in the photographs are as close as possible with the photographic and printing technology utilized and the color values cited in the Detailed Botanical Description accurately describe the colors of the new *Coreopsis*.

DETAILED BOTANICAL DESCRIPTION

The following is a detailed description of 3 month-old plants of the new cultivar as grown outdoors in 13-cm containers in Boskoop, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Early summer to late summer in The Netherlands.

*Plant type*.—Herbaceous perennial.

*Plant habit*.—Dwarf and upright.

*Height and spread*.—An average of 20.6 cm in height and 22.6 cm in width.

*Cold hardiness*.—At least to U.S.D.A Zone 4.

*Diseases and pests*.—No susceptibility or resistance to diseases or pests has been observed.

*Root description*.—Fibrous when young, becoming fleshy with age, 162D in color.

*Root development*.—An average of 10 days for root initiation and about 5 weeks to produce a young rooted plant in a 10-cm container.

*Propagation*.—Stem cuttings.

*Growth rate*.—Moderate.

Stem description:

*Shape*.—Oval and slightly ridged.

*Stem color*.—143A to 143B.

*Stem size*.—An average of 5.4 cm in length (excluding inflorescence) and 1.5 mm in diameter.

*Stem surface*.—Glabrous, glossy, slightly axially ribbed.

*Stem aspect*.—Upward and outward.

*Stem strength*.—Strong.

*Branching habit*.—Well-branched, an average of 32 lateral branches.

*Internode length*.—An average of 2.5 cm.

Foliage description:

*Leaf division*.—Simple.

*Leaf margins*.—Entire.

*Leaf size*.—An average of 4.5 cm in length and 3 mm in width.

*Leaf shape*.—Narrow lanceolate.

*Leaf base*.—Narrow cuneate.

*Leaf apex*.—Acute.

*Leaf venation*.—Pinnate, color; upper surface 137B and lower surface 144A.

*Leaf attachment*.—Sessile.

*Leaf arrangement*.—Opposite.

*Leaf surface*.—Both surfaces dull and glabrous.

*Leaf color*.—Young upper surface; 137B, young lower surface; 143B, mature upper surface 137A to 137B, mature lower surface 143A.

*Leaf number*.—An average of 6 leaves (3 pairs) per stem.

Inflorescence description:

*Inflorescence type*.—Terminal capitulate, with a single row of ray florets surrounding disk florets in the center.

*Lastingness of inflorescence*.—An average of 3 weeks, self-cleaning.

*Fragrance*.—Moderate to faint, of musk and straw.

*Quantity of inflorescences*.—An average of 1 per lateral branch.

*Inflorescence size*.—An average of 3.7 cm in diameter and 1 cm in height, disk portion an average of 8 mm in diameter.

*Inflorescence buds*.—An average of 5 mm in depth and diameter, globular in shape, color; 143B with apex 152B and longitudinal stripes 200D.

*Peduncle*.—Primary; an average of 6.9 cm in length and 1 mm in width, held straight upright, secondary; an average of 5.8 cm in length and 1 mm in width, held at an average angle of 20° to primary peduncle, slightly glossy and glabrous on all surfaces and 143B in color.

Involucral bracts:

*Bract number*.—Two rows of 8.

*Bract arrangement*.—Rotate.

*Bract size*.—Outer bracts; an average of 3 mm in length and 2 mm in width, inner bracts; an average of 7 mm in length and 4 mm in width.

*Bract color*.—Inner bracts; 22A with base 146A and outer bracts; 143A.

*Bract texture*.—Glabrous and slightly glossy on outer and inner surfaces of outer and inner bracts.

*Bract apex*.—Acute on outer and inner bracts.

*Bract base*.—Broadly cuneate on inner and outer bracts.

*Bract margins*.—Entire.

*Bract shape*.—Outer bracts; narrow ovate, inner bracts; ovate.

Ray florets (sterile):

*Number*.—An average of 8 arranged primarily in one row.

*Shape*.—Obovate.

*Size*.—An average of 1.8 cm in length and 9 mm in width.

*Apex*.—Irregularly lobed with an average of 3 acute lobes, center lobe is about 2 mm longer than the lateral lobes.

*Base*.—Cuneate.

*Margins*.—Entire with apex lobed.

*Aspect*.—Held horizontal to slightly upward.

*Texture*.—Glabrous and velvety on both surfaces, outer surface is moderately carinate.

*Color*.—Upper surface when opening; 59A with margins N66C to N66D, lower surface when opening; 182C with base 183C, upper surface when open; a blend between 59A and 187B, lower surface when open; 183D, color not fading.

*Petaloids*.—Ray floret like, 0 to 3 per inflorescence, an average of 4 mm in length and 2 mm in width, narrow obovate in shape, rounded apex, cuneate base, coloration matches ray floret color.

Disk florets (perfect):

*Shape*.—Tubular, spirally arranged on disc.

*Apex*.—Acute.

*Base*.—Lower 87.5% fused into tube.

*Number*.—About 100.

*Size*.—An average of 4 mm in length and 1.2 mm in width at the apex and 0.4 mm in width at the base.

*Texture*.—Glabrous and velvety on both surfaces.

*Color*.—En masse; N25A, corolla; base of tube is 16A to 16B in color, flared portion is N25A.

*Receptacle*.—An average of 1.5 mm in diameter and depth, 143B in color.

Reproductive organs:

*Presence*.—Disk florets are perfect, ray florets are sterile.

*Gynoecium*.—Pistil; 1, an average of 2.5 mm in length, style; an average of 2 mm in length and 16A in color, stigma; decurrent and 23A in color, ovary; 151C in color.

*Androecium*.—Stamens; 5, anther; basifixed and linear in shape, an average of 1.5 mm in length and 203D in color, pollen; moderate in quantity and 17A in color.

*Fruit/seed*.—No fruit or seed development was observed.

It is claimed:

1. A new and distinct cultivar of *Coreopsis* plant named 'URIBL01' as herein illustrated and described.

* * * * *